United States Patent [19]

Hirohara et al.

[11] 4,255,521

[45] Mar. 10, 1981

[54] METHOD FOR ISOLATION OF GLUCOSE ISOMERASE

[75] Inventors: Hideo Hirohara; Shigeyasu Nabeshima; Satoshi Mitsuda, all of Ibaraki; Tsuneyuki Nagase, Takatsuki, all of Japan

[73] Assignee: Sumitomo Chemical Company, Limited, Osaka, Japan

[21] Appl. No.: 40,872

[22] Filed: May 21, 1979

[30] Foreign Application Priority Data

May 25, 1978 [JP] Japan .................................. 53/62893

[51] Int. Cl.$^3$ ................................................ C12N 9/92
[52] U.S. Cl. .................................... 435/234; 435/803; 435/886; 435/887
[58] Field of Search ................. 435/234, 233, 259, 803

[56] References Cited

U.S. PATENT DOCUMENTS

| | | | |
|---|---|---|---|
| 3,980,521 | 9/1976 | Amotz et al. | 435/259 |
| 4,077,842 | 3/1978 | Cory | 435/233 |

*Primary Examiner*—Lionel M. Shapiro
*Attorney, Agent, or Firm*—Cushman, Darby & Cushman

[57] ABSTRACT

In a process for extracting glucose isomerase from microorganism cells containing glucose isomerase by the so called high pressure release and impact method in which the suspension of the microorganism cells is homogenized for the extraction by releasing the pressure applied on said suspension instantaneously and giving the suspension an impact at very high velocity, the concentration of the suspension containing microorganism cells and the pressure applied on the said suspension are selected within specific ranges, namely from 0.5 to 10 wt. % (on a dry substance base) and from 400 to 700 Kg/cm$^2$, respectively.

9 Claims, No Drawings

METHOD FOR ISOLATION OF GLUCOSE ISOMERASE

The present invention relates to a process for extracting glucose isomerase, more particularly, the invention pertains to an improved method for extracting glucose isomerase from microorganisms possessing glucose isomerase activity in their cells.

Glucose isomerase is a general name of an enzyme which catalyzes reversible mutual conversions between glucose and fructose.

The enzyme, which is an intracellular enzyme found in various microorganisms, is commercially used for production of a high fructose corn syrup by isomerization of glucose. In practical application of the enzyme in the prior art, there has been generally used the batch method wherein the microorganisms producing said enzyme are directly, or at most after heat-treatment of the cells to prevent the enzyme components from being released from the cells, thrown into a reaction vessel. According to this method, the reaction time is long whereby the product is colored, and the times for utilization of cells are very few. For overcoming these drawbacks, there has recently applied the method in which isomerization reaction is continuously conducted using glucose isomerase which is immobilized by various methods. Immobilization of glucose isomerase can be classified broadly into two methods according to the state of glucose isomerase to be immobilized. In one method, the microorganism producing said enzyme is immobilized, while glucose isomerase extracted from the microorganism cells is immobilized in the other. Although both methods cannot be free from advantages and disadvantages, the latter method is advantageous in that there can be obtained an enzyme with higher activity per unit weight of immobilized enzyme, that the extracted enzyme is stable and also that there can be obtained immobilized enzyme with higher productivity. Thus, it is of a great commercial significance to find out a method by which a large amount of enzymes can be extracted within a short time. As the methods for the rupture of microorganism cells to yield active enzyme preparations, there have generally been known several methods such as ultra-sonic wave method, freezing and thawing method, self-digestion (autolysis) method, grinding method, high pressure release method, lysozyme treatment method, and mechanical shaking with abrasives. All of these methods are generally applicable for extraction of glucose isomerase.

The present inventors have made extensive studies over the above methods for the rupture of microorganism cells to extract active glucose isomerase (see Table 1). Consequently, the high pressure release and impact method which consists in forcing a suspension of the microorganism cells at high pressure, releasing it through an aperture where an instantaneous pressure drop occures and then giving it an impact is found to be short in time for treatment of the microorganism cells, high in activity recovery [activity recovery (%)=(total activity of the supernatant from which the microorganism cells are removed by centrifugation at 10,000 G for 10 minutes of the homogenized extract)/(total activity of the suspension of the microorganism cells before homogenization)×100] and also advantageous to treatment of a large amount of microorganism cells commercially. As the result of further extensive studies over this method, it has now been found that the extraction efficiency of glucose isomerase depends greatly on the concentration of the suspension of the microorganism cell and the pressure employed, that a crude enzyme solution of glucose isomerase can be obtained at 100% or more of activity recovery by suitable selection of the suspension concentration and the pressure, and further that the microorganism cells can also be separated with ease after the extraction. The present invention has been accomplished based on such findings. That is, by using the high pressure release and impact method wherein the concentration of the suspension of microorganism cells is controlled at 0.5 to 10 wt.% (on a dry substance base) and the pressure employed at 400 to 700 $Kg/cm^2$, glucose isomerase can be extracted efficiently from the microorganism cells containing glucose isomerase.

TABLE I

Various extraction methods investigated

| Extraction method | Instrument or reagent used (manufacturer) | Suspension volume (ml)* | Treatment time (hrs) | Other conditions | Activity recovery (%)** |
|---|---|---|---|---|---|
| Lysozyme treatment | Egg white lysozyme recrystallized 3 times (Tokyo Kasei) | 1,000 | 4 | 100 mfg, 40° C. | 91.0 |
| Self-digestion | Toluene | 500 | 24 | left to overnight at 15"20° C. | 46.6 |
| Mechanical shaking with abrasives | Ball mill | 500 | 10 | 900 rpm, 500 g of beads used | 99.5 |
| | Waring blender | 50 | 0.33 | about 50 g of sea sand used | 41.7 |
| | Mixer (Nippon Seiki Seisakusho) | 100 | 1.0 | about 100 g of sea sand used | 95.6 |
| Grinding | Rotatory type grindstone homogenizer (Tokushukika | 1,000 | 1.0 | Grindston interval: 0.2mm | 95.9 |

TABLE I-continued

| Extraction method | Instrument or reagent used (manufacturer) | Suspension volume (ml)* | Treatment time (hrs) | Other conditions | Activity recovery (%)** |
|---|---|---|---|---|---|
| Ultra-sonic wave | Kogyo) Ulra-sonic generator (Kubota Shoji) | 100 | 0.25 | 9 KHz | 118.6 |
| High pressure release and impact method (present method) | Gaulin homogenizer (Gaulin Corp.) | 1,000 | 0.02 | pressure: 550 kg/cm$^2$ | 106.0 |

*The concentrations of the suspensions of the microorganism cells are all 5 wt. %.
**Activity recovery (%) = (total activity of the supernatant from which the microorganism cells are removed by centrifugation at 10,000 G for 10 minutes of the homogenized extract)/(total activity of the suspensions ofthe microorganism cells befoe homogenization) × 100

An operational principle may be described as follows: A suspension of the microorganism cells with a concentration of 0.5 to 10% (on a dry substance base) is forced to enter a valve area at a pressure of 400 to 700 Kg/cm$^2$. The pressure forces open the pre-loaded adjustable valve and the suspension through the aperture where an instantaneous (less than 10 $\mu$sec.) pressure drop to less than an atmosphere occurs, causing shearing action and cavitation bubbles, which causes disruption of the cell particles to much smaller size. The suspension product then strikes the impact ring at a velocity of more than 15 km/min., further shattering the particles by impact. The suspension of the microorganism cell is thus homogenized efficiently to result in the extraction of glucose isomerase at an activity recovery of 100% or more under some conditions. The homogenized suspension product is discharged at a pressure sufficient for movement. The fact that the activity recovery as defined hereinabove can be 100% or more evidences the fact that the extraction of the enzyme is advantageous from standpoint of commercial utilization of glucose isomerase. When the suspension of the microorganism cell is more dilute, the enzyme can be extracted at relatively lower pressure. But an amount of the extract becomes large, whereby it may take a long time in order to separate microorganism cells and to obtain a concentrated crude enzyme solution. High pressure on a dilute suspension will lead to breaking of the cells to unnecessarily small sizes, whereby the disrupted microorganism cells may become separable with great difficulty and the extracted enzyme tends to be lowered in specific activity. On the other hand, in case of a highly concentrated suspension of the microorganism cells, no sufficient extraction of the enzyme can be effected unless a very high pressure is applied thereon or the treatments said above are repeated for many times. In short, the concentration of the suspension of the microorganism cells and the pressure to be applied should be so selected as to be well balanced. The range for the concentration of the suspension and the pressure range as specified above are selected as commercially advantageous conditions after extensive studies. Particularly, it is preferred to control the concentration of the suspension of microorganism cells to be 1.5 to 6 wt.% and the pressure applied to be 450 to 600 Kg/cm$^2$, whereby it is possible to obtain a glucose isomerase solution at an activity recovery of 100% or more continuously with good efficiency by one cycle of the pressure application-pressure drop-impact operation.

The microorganism cells cultivated may be provided for suspensions without any specific treatment, or they are once separated from the culture broth, and are subjected to freezing or heating treatment, then they are formed into suspensions. The water to be used for suspending microorganism cells may either be tap water, deionized water or distilled water. For stability of the enzyme, deionized water or distilled water may preferably be used. For adjusting pH of the suspension, a buffer solution may be used and it is preferred to add magnesium ions with concentration of $1 \times 10^{-4}$ M to $5 \times 10^{-3}$ M from standpoint of improving stability and activity of the enzyme. The suspension is generally adjusted at pH 6.0 to 10.0, preferably at 7.0 to 9.0. The temperature at which the extraction is effected is desirably 10° to 60° C.

Commercially utilized glucose isomerase is found primarily in cells of microorganisms belonging to the genus Streptomyces. The extraction method according to the present invention may be applicable for microorganisms belonging to the genus Streptomyces capable of producing glucose isomerase, including *Streptomyces phaeochromogenes, Streptomyces albus, Streptomyces roseochromogenus, Streptomyces wedmorensis, Streptomyces flavovirens, Streptomyces achromogenes*, etc.

As commercially available homogenizer which coincides with the requirements for the extraction of glucose isomerase of the present invention, there may be mentioned, for example, Gaulin homogenizer (produced by Gaulin Corp.). By means of this homogenizer, it is possible to extract glucose isomerase by homogenization of about 50 liters to about 9000 liters of the suspensions of the microorganism cell per hour according to the treatment cycle comprising (1) suction of the fluid to be treated→(2) pressure application→(3) pressure drop→(4) impact→(5) discharge, which is to be operated at the pressure of 400 to 700 Kg/cm$^2$ by varying the horse power of the motor.

Pressure applied on the suspension of the microorganism cell is generally effected by means of a plunger pump, so that it is relatively easy to homogenize a large amount of the suspension in a short time by the continuous operation of the treatment cycle said above.

When the concentration of the suspension of the microorganism cell is from 0.5 to 10 wt.% (on dry substance base), it is possible to extract glucose isomerase at an activity recovery of 80% or more by the one treatment cycle said above or by repeating the same cycle for a few times for the same suspension. It is particularly preferred to use a suspension of the microorganism cells with a concentration of 1.5 to 6 wt.% (on a dry substance base). By conducting the treatment operation of one cycle continuously at a pressure of 450 to 600 Kg/cm$^2$, a large amount of glucose isomerase can be extracted within a short time at an activity recovery of 100% or more.

The present invention is further illustrated below with reference to the Examples, which are set forth only for illustrative purpose, and it should be interpreted that the present invention is not limited by these Examples but various modifications are possible within the spirit of the invention. In the Examples, the activity of glucose isomerase, protein content and fructose content are determined according to the following methods:

(1) Activity assay

To a glucose isomerase solution are added a 0.1 M D-glucose solution, a 0.05 M phosphate buffer solution and a 0.005 M MgSO$_4$.7H$_2$O solution. While maintaining at pH 7.0, the reaction is continued at 70° C. for one hour and the amount of fructose produced is measured. The unit of activity is expressed in terms of "unit" and the amount of enzyme which produces 1 mg of fructose under the above conditions is defined as 1 unit.

(2) Measurement of fructose content

The fructose content is quantitatively determined from absorption strength at 560 nm after 30 minutes by cysteine-carbazol-sulfuric acid method at 30° C. Under these conditions, the degree of color formation of glucose is as small as about 1/200 of that of fructose, and therefore color formation by glucose is negligible.

(3) Quantitative determination of protein content

A quantitative determination of protein content is made by Lowry method with reference to "Biochemistry Experiment Course", vol. 5, p. 27. The calibration curve is made using crystallized bovine serum albumin (250 μg/ml solution).

EXAMPLE 1

Five kilograms of freezed wet microorganism cells (moisture content: 57%) containing glucose isomerase (Streptomyces phaeochromogenes, produced by Nagase Sangyo Co.) are suspended in 5×10$^{-3}$ M phosphate buffer (pH 7.5, containing 5×10$^{-4}$ M Mg$^{++}$ ions) to make up the total amount of 50 Kg. The total activity of the suspension of the microorganism cells is found to be 8.04×10$^6$ unit. This suspension is subjected to continuous homogenization by Gaulin homogenizer-model 15 M (produced by Gaulin Co.) to extract glucose isomerase therefrom. The total activity of the supernatant obtained by centrifugation of microorganism cells from the extract is found to be 8.44×10$^6$ unit, the activity recovery being 105%. The pressure applied on the suspension of the microorganism cell is 550 Kg/cm$^2$, the time required for homogenization of the total suspension about 55 minutes and the temperature room temperature (about 20° C.).

EXAMPLE 2

Cultured living microorganism cells (178 g as wet base, Ca. 85 g on a dry substance base) of Streptomyces albus ATCC No. 21132 (YT No. 5) are suspended in deionized water, containing 5×10$^{-4}$ M Mg$^{++}$ ions and being adjusted at pH 7.3, to make up the total volume of 1280 ml. The total activity of the suspension is found to be 2.5×10$^5$ unit. By homogenizing this suspension by Gaulin homogenizer-model 15 M at pressure of 560 Kg/cm$^2$, glucose isomerase is extracted therefrom. The treatment time is about one minute and a half. A part of the extract (about 10 ml) is sampled and, after centrifugal separation, the resultant supernatant is measured for protein concentration and activity, from which the total activity and the activity recovery are calculated. The homogenized fluid is again subjected to repeated homogenization twice under the same homogenization conditions for the first cycle and each supernatant is measured for protein concentration and activity, from which the activity recovery is calculated. The results are shown together in Table 2. The treatment is made at room temperature (about 20° C.).

TABLE 2

| Time of pressure difference treatments | Enzyme activity (unit/ml) | Protein concentration (mg/ml) | Specific activity (unit/mg-protein) | Total activity (unit) | Activity recovery (%) |
|---|---|---|---|---|---|
| 1 | 174 | 2.79 | 62.4 | 2.23 × 10$^5$ | 8.90 |
| 2 | 203 | 3.33 | 61.0 | 2.60 × 10$^5$ | 104 |
| 3 | 210 | 3.90 | 53.8 | 2.69 × 5 | 108 |

In the above experiment, cultivation of Streptomyces albus is performed according to conventional method, as is disclosed, for example, by Japanese published examined patent application No. 16352/1969.

Using the same freezed wet microorganism cells (moisture content: 57%) as used in Example 1, the microorganism cells are suspended in 5×10$^{-3}$ M phosphate buffer containing 5×10$^{-3}$ M Mg$^{++}$ ions. Extractions of this suspension are carried out by Gaulin homogenizer-model 15 M at room temperature (about 20° C.) according to only one cycle treatment. The conditions and the results are shown in Table 3.

TABLE 3

| | Suspension | | Treatment conditions | | Results | | |
|---|---|---|---|---|---|---|---|
| Example No. | Conc. amount (kg cells/kg) | Total activity of cells (unit) | Pressure (Kg/cm$^2$) | Treatment time (min.) | Specific activity (unit/g-protein) | Total activity (unit) | Activity recovery (%) |
| 3 | 2/35.5 | 3.2 × 10$^6$ | 500 | ca.35 | 39.2 | 4.3 × 10$^6$ | 134 |
| 4 | 2/30 | 3.2 × 10$^6$ | 500 | ca.30 | 48.9 | 3.6 × 10$^6$ | 113 |

We claim:

1. A process for extracting glucose isomerase from cells of microorganisms of the geneus Streptomyces containing glucose isomerase, which comprises carrying out a continuous homogenization operation for the extraction by means of the cycle of (i) suction of a suspension of the microorganism cells, (ii) application of the pressure on the suspension, (iii) instantaneous pressure drop to less than an atmosphere by passing through a aperture, (iv) impact of the suspension particles to walls and (v) the discharge of the homogenized product, wherein the concentration of the suspension of the microorganism cells is from 1.5 to 6 weight % on a dry substance base and the pressure is from 450 to 600 Kg/cm$^2$.

2. A process for extracting glucose isomerase according to claim 1, wherein the suspension of the microorganism cells includes magnesium ions with concentration of $1 \times 10^{-4}$ M to $5 \times 10^{-3}$ M.

3. A process for extracting glucose isomerase according to claim 1, wherein pH of the suspension of the microorganism cells is in the range of 7.0 to 9.0.

4. A process for extracting glucose isomerase according to claim 1, wherein the temperature of the extraction is in the range of 10° C. to 60° C.

5. A process for extracting glucose isomerase according to claim 1, wherein the microorganism is *Stretomyces phaeochromogenes*, *Streptomyces albus*, *Stretomyces roseochromogenes*, *Streptomyces wedmorensis*, *Streptomyces flavorirens*, or *Streptomyces achromogenes*.

6. A process for extracting glucose isomerase according to claim 1, wherein the microorganism is *Streptomyces phaeochromogenes*, or *Streptomyces albus*.

7. A process for extracting glucose isomerase according to claim 1, wherein the pressure applied on the suspension is effected by means of a plunger pump.

8. A process for extracting glucose isomerase according to claim 1, wherein the pressure drop to less than an atmosphere is achieved within a time of less than 10 μsec.

9. A process for extracting glucose isomerase according to claim 1, wherein impact of the suspension particles to walls occurs at a velocity of more than 15 Km/min.

* * * * *